(12) United States Patent
Hypolite et al.

(10) Patent No.: US 9,880,131 B2
(45) Date of Patent: Jan. 30, 2018

(54) LIQUID-LIQUID SEPARATOR INTERFACE DETECTION SYSTEM AND POLYMERIZATION PROCESS UTILIZING THE SAME

(75) Inventors: Curvel Hypolite, Rosharon, TX (US); Alec Y. Wang, Lake Jackson, TX (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 1014 days.

(21) Appl. No.: 13/467,845

(22) Filed: May 9, 2012

(65) Prior Publication Data

US 2012/0277392 A1 Nov. 1, 2012

Related U.S. Application Data

(63) Continuation-in-part of application No. 13/377,920, filed as application No. PCT/US2010/042139 on Jul. 15, 2010.

(51) Int. Cl.
| | | |
|---|---|---|
| *G01S 5/18* | (2006.01) | |
| *C08F 6/12* | (2006.01) | |
| *G01N 29/024* | (2006.01) | |
| *C08F 2/01* | (2006.01) | |
| *C08F 2/06* | (2006.01) | |

(Continued)

(52) U.S. Cl.
CPC .............. *G01N 29/024* (2013.01); *C08F 2/01* (2013.01); *C08F 2/06* (2013.01); *C08F 2/14* (2013.01); *C08F 6/12* (2013.01); *C08J 11/02* (2013.01); *G01F 23/296* (2013.01); *G01N 29/02* (2013.01); *G01N 29/223* (2013.01);

(Continued)

(58) Field of Classification Search
None
See application file for complete search history.

(56) References Cited

U.S. PATENT DOCUMENTS

| 2,945,016 A | 7/1960 | Benedict |
| 3,553,156 A | 1/1971 | Anolick et al. |

(Continued)

FOREIGN PATENT DOCUMENTS

| CA | 2644410 | 2/2009 | |
| DE | 10325953 A1 * | 12/2004 | ........... G01F 23/296 |

(Continued)

OTHER PUBLICATIONS

Jared Ledgard, Kings Chem Guide, 2006.*

(Continued)

*Primary Examiner* — Richard A Huhn
(74) *Attorney, Agent, or Firm* — Cantor Colburn LLP

(57) ABSTRACT

A system for detecting an interface between polymer-rich phase and solvent-rich phase comprising a liquid-liquid separator configured to receive a polymer solution as an inlet stream produced in a solvent-based polymerization reactor through an inlet feed, wherein the tank is configured to permit the stream to separate into a polymer rich phase and a solvent rich phase; a first sonic transponder for sending a first sonic signal from either a top or bottom of the liquid-liquid separator and for receiving a first reflected portion of the sonic signal, the reflected portion of the sonic signal created by the passage of the sonic signal through a liquid-liquid interface between the solvent rich phase and the polymer rich phase is provided.

6 Claims, 2 Drawing Sheets

(51) Int. Cl.
*C08F 2/14* (2006.01)
*G01N 29/02* (2006.01)
*C08J 11/02* (2006.01)
*G01N 29/22* (2006.01)
*G01F 23/296* (2006.01)

(52) U.S. Cl.
CPC ........... *G01N 2291/0222* (2013.01); *G01N 2291/0251* (2013.01); *G01N 2291/051* (2013.01); *G01S 5/18* (2013.01)

(56) References Cited

U.S. PATENT DOCUMENTS

| | | | |
|---|---|---|---|
| 4,319,021 | A | 3/1982 | Irani et al. |
| 4,623,712 | A | 11/1986 | Irani et al. |
| 5,142,504 | A | 8/1992 | Koester et al. |
| 6,212,943 | B1 | 4/2001 | Maltby et al. |
| 6,881,800 | B2 | 4/2005 | Friedersdorf |
| 9,327,221 | B2 | 5/2016 | Hypolite et al. |
| 2004/0136271 | A1 | 7/2004 | Gluszyk |
| 2008/0153996 | A1* | 6/2008 | Friedersdorf et al. .......... 526/68 |
| 2011/0112773 | A1 | 5/2011 | Atkinson |
| 2012/0088893 | A1 | 4/2012 | Jog et al. |
| 2012/0277392 | A1 | 11/2012 | Hypolite et al. |

FOREIGN PATENT DOCUMENTS

| | | |
|---|---|---|
| GB | 2472083 | 1/2011 |
| WO | 9957527 | 11/1999 |
| WO | WO2006044149 | 4/2006 |

OTHER PUBLICATIONS

EP Office Action dated Dec. 16, 2014; from EP counterpart Application No. 13717355.5.
EP Response to Office Action dated May 19, 2015; from EP counterpart Application No. 13717355.5.
International Search Report for International Application No. PCT/US2010/042139, International Filing Date Jul. 15, 2010, dated Sep. 13, 2010; 4 pages.
International Search Report for International Application No. PCT/US2013/031163, International Filing Date Mar. 14, 2013, dated Jun. 17, 2013; 4 pages.
Written Opinion for International Application No. PCT/US2010/042139, International Filing Date Jul. 15, 2010, dated Sep. 13, 2010; 5 pages.
Written Opinion for International Application No. PCT/US2013/031163, International Filing Date Mar. 14, 2013, dated Jun. 17, 2013; 6 pages.

\* cited by examiner

LIQUID-LIQUID SEPARATOR INTERFACE DETECTION SYSTEM AND POLYMERIZATION PROCESS UTILIZING THE SAME

This application is a continuation-in-part of application Ser. No. 13/377,920, filed on Dec. 13, 2011, which was a National Stage Entry of PCT/US10/42139 filed on Jul. 15, 2010, which is incorporated by reference in its entirety.

FIELD OF INVENTION

The instant invention relates to a liquid-liquid separator interface detection system and polymerization process utilizing same.

BACKGROUND OF THE INVENTION

Liquid-liquid separators are used in a variety of applications to separate two liquid phases having different densities. Liquid-liquid separators may be used to separate the solvent and polymer in the Solution Polyolefin process. For the stability of a solution, it is very important to control the interface layer (the rag layer) between the polymer solution and pure solvent. The location of this layer determines the degree of separation between the two liquids. Unfortunately, the separator does not contain any side glass to view the interface and a sonic probe was used to detect the polymer and solvent interface in the carbon steel vessel.

SUMMARY OF THE INVENTION

The instant invention is a liquid-liquid separator interface detection system and polymerization process utilizing same.

In one embodiment, the instant invention provides a system for detecting an interface between a polymer-rich phase and a solvent-rich phase comprising a liquid-liquid separator (LLS) configured to receive an inlet stream comprising solvent, polymer and unreacted monomer produced in a solvent-based polymerization reactor through an inlet feed, wherein the tank is configured to provide a residence time of at least 20 minutes and to permit the stream to separate into a polymer rich phase and a solvent rich phase; a first sonic transponder for sending a first sonic signal from either a top or bottom of the liquid-liquid separator and for receiving a first reflected portion of the sonic signal, the reflected portion of the sonic signal created by the passage of the sonic signal through a liquid-liquid interface between the solvent rich phase and the polymer rich phase, wherein the first sonic transponder is positioned such that it transmits a signal with travels perpendicularly to the liquid-liquid interface.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

DETAILED DESCRIPTION OF THE INVENTION

Figure 1:
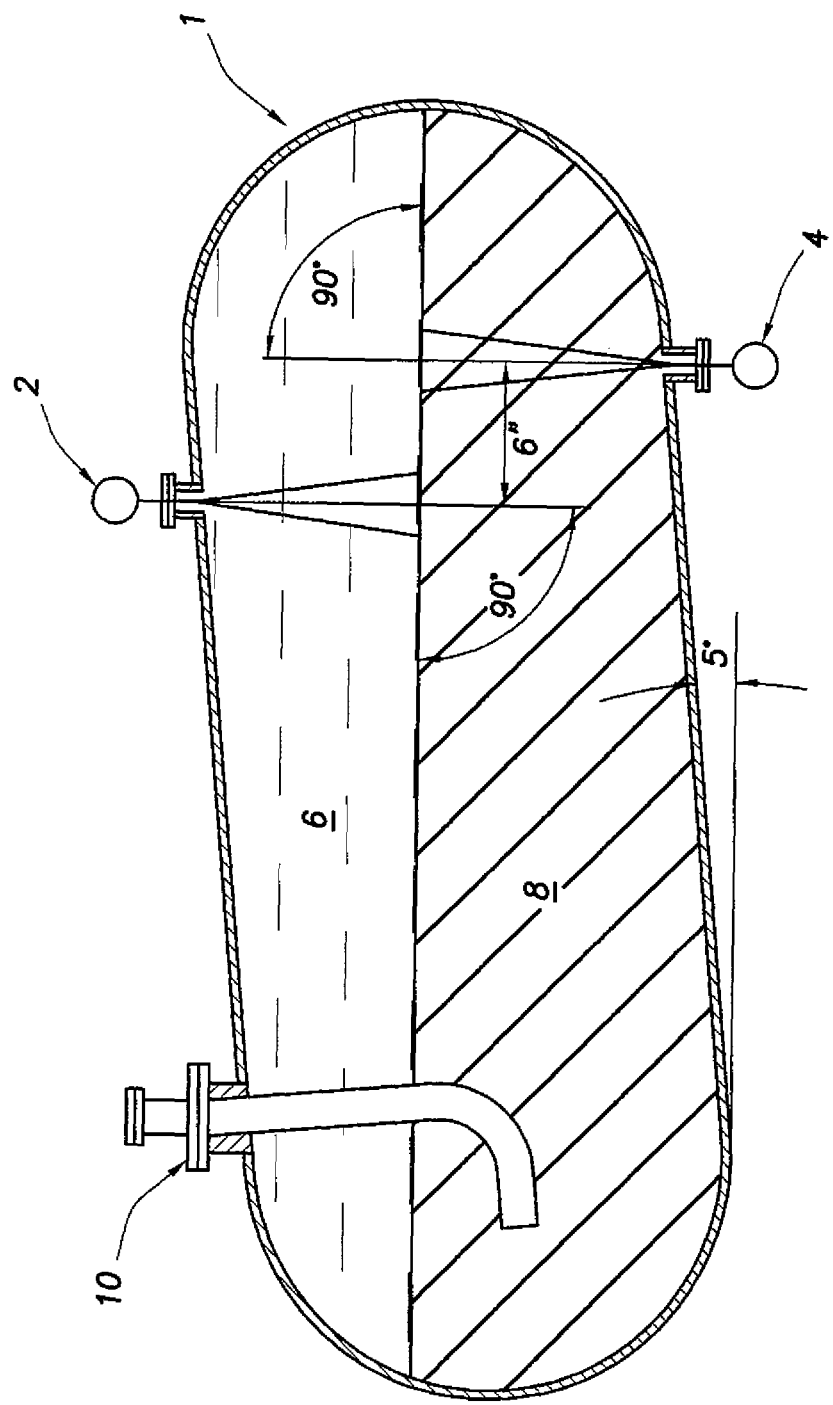
FIG. 1 is a schematic of a liquid-liquid separator with two sonic transponders according to an embodiment of the invention.

The instant invention is a liquid-liquid separator interface detection and control system and polymerization process utilizing same.

The liquid-liquid separator interface detection system according to the present invention comprises: a liquid-liquid separator (LLS) configured to receive polymer solution as an inlet stream comprising solvent, polymer and unreacted monomer produced in a solvent-based polymerization reactor through an inlet feed, wherein the tank is configured to provide a residence time of at least 20 minutes and to permit the stream to separate into a polymer rich phase and a solvent rich phase; a first sonic transponder for sending a first sonic signal from either a top or bottom of the liquid-liquid separator and for receiving a first reflected portion of the sonic signal, the reflected portion of the sonic signal created by the passage of the sonic signal through a liquid-liquid interface between the solvent rich phase and the polymer rich phase, wherein the first sonic transponder is positioned such that it transmits a signal with travels perpendicularly to the liquid-liquid interface.

Liquid-liquid separator systems generally of use in embodiments of the invention are generally described in U.S. Patent Application Publication No. 20120088893, the disclosure of which is incorporated herein by reference. As discussed therein, a liquid-liquid separator may be used to remove solvent from polymer solution by using the phenomenon of Lower Critical Solution Temperature (LCST) in the solution polymerization process. The present invention relates to the use of a sonic transponder to detect the location of the liquid-liquid interface between the polymer-rich phase and the solvent-rich phase.

The polymerization process according to the instant invention comprises: A) polymerizing one or more monomers in the presence of a reaction solvent, to form a polymer solution; B) transferring the polymer solution as an inlet stream into a liquid-liquid separator, without adding heat to the solution, and wherein the pressure of the polymer solution is actively reduced in a controlled manner prior to, or within, the liquid-liquid separator, to induce at least two liquid phases, a polymer-rich phase and a solvent-rich phase, and wherein the concentration of polymer in the polymer-rich phase is higher than that in the polymer solution transferred to the liquid-liquid separator; and C) detecting an interface between the polymer-rich phase and the solvent-rich phase by use of a sonic transponder positioned within the liquid-liquid separator; and D) removing one or both of the solvent-rich phase and the polymer-rich phase.

In an alternative embodiment, the instant invention provides a liquid-liquid separator interface detection system and polymerization process, in accordance with any of the preceding embodiments, except that polymer solution has a residence time in the LLS of at least 20 minutes. All individual values and subranges from at least 20 minutes are included herein and disclosed herein; for example, the residence time can be from a lower limit of 20, 24, 28, 32, 36, or 40 minutes. For example, the residence time may be from at least 20 minutes, or in the alternative, the residence time may be from at least 30 minutes or in the alternative, the residence time may be from at least 40 minutes. The residence time is the average amount of time a fluid (typically two phases) spends in the LLS. This time is calculated as the ratio of the "volume of the LLS vessel"/"volumetric flow rate of the inlet stream into the LLS."

In an alternative embodiment, the instant invention provides a liquid-liquid separator interface detection system and polymerization process, in accordance with any of the preceding embodiments, except that the first sonic transponder is enclosed partially in a sleeve. In such embodiments, the sleeve is configured and placed so that it does not interrupt or impact the path of the soundwave generated by the sonic transponder.

In an alternative embodiment, the instant invention provides a liquid-liquid separator interface detection system and polymerization process, in accordance with any of the preceding embodiments, except that the inlet feed feeds the polymer solution into a bottom portion of the liquid-liquid separator.

In an alternative embodiment, the instant invention provides a liquid-liquid separator interface detection system and polymerization process, in accordance with any of the preceding embodiments, except that the liquid-liquid separator is jacketed.

In an alternative embodiment, the instant invention provides a liquid-liquid separator interface detection system and polymerization process, in accordance with any of the preceding embodiments, except that the liquid-liquid separator is a gravity separator.

In an alternative embodiment, the instant invention provides a liquid-liquid separator interface detection system and polymerization process, in accordance with any of the preceding embodiments, except that the system further comprises a polymer rich phase outlet valve comprising a flow meter and a differential pressure transmitter located on either side of the flow meter.

In an alternative embodiment, the instant invention provides a liquid-liquid separator interface detection system and polymerization process, in accordance with any of the preceding embodiments, except that the system further comprises an automated control valve to control the level of polymer rich phase in the liquid-liquid separator.

In an alternative embodiment, the instant invention provides a liquid-liquid separator interface detection system and polymerization process, in accordance with any of the preceding embodiments, except that the system further comprises a second sonic transponder for sending a second sonic signal from either a top or bottom of the liquid-liquid separator and for receiving a second reflected portion of the sonic signal.

In an alternative embodiment, the instant invention provides a liquid-liquid separator interface detection system and polymerization process, in accordance with any of the preceding embodiments, except that the system further comprises a control system to receive and analyze data recovered from the first, and optionally from the second, sonic transponders.

Sonic transponders and control systems therefor are known in the art and are commercially available. One exemplary commercially available sonic transponder and control system is available under the trade name INTERFAZER from Transducer USA (Houston, Tex.).

As used herein, the term "sonic transponder" means a device including both a sound transmitter and a sound receiver. Sonic transponders are useful in the inventive system and process and are based on the principles of active SONAR. Active sonar creates a pulse of sound, a soundwave, and then detects reflections of the pulse. This pulse of sound is generally created electronically using a sonar projector consisting of a signal generator, power amplifier and electro-acoustic transducer/array. A beamformer may be employed to concentrate the acoustic power into a beam. A portion of the sound wave is reflected from an interface between two liquid phases having different densities or between liquid and solid phases. The reflected portion is received by the sonic transponder and the distance to the interface may be calculated using known principles based on the speed of sound in liquids. Commercial systems, such as the INTERFAZER, typically include the standard electronics and software for converting reflected sound waves into electronic signals and for calculating the location of the interface which generated a reflected sound wave.

In an alternative embodiment, the instant invention provides a liquid-liquid separator interface detection system and polymerization process, in accordance with any of the preceding embodiments, except that the sonic transponder provides continuous interface detection.

In an alternative embodiment, the instant invention provides a liquid-liquid separator interface detection system and polymerization process, in accordance with any of the preceding embodiments, except that the sonic transponder provides intermittent interface detection. In such embodiments, the sonic transponder may send and receive signals at specified time intervals or on demand.

In an alternative embodiment, the instant invention provides a liquid-liquid separator interface detection system and polymerization process, in accordance with any of the preceding embodiments, except that the reaction solvent is a mixture of a heavy hydrocarbon solvent (for example, containing a $C_6$-$C_{10}$ hydrocarbon component) and a light hydrocarbon solvent (for example, containing a $C_2$-$C_5$ hydrocarbon component). The liquid-liquid separation can be achieved by dropping pressure, thereby inducing the formation of two phases, polymer-rich and solvent-rich liquid phases.

In an alternative embodiment, the instant invention provides a liquid-liquid separator interface detection system and polymerization process, in accordance with any of the preceding embodiments, except that the heavy hydrocarbon solvent comprises at least one hydrocarbon containing from 6 to 10 carbon atoms. In an alternative embodiment, the at least one hydrocarbon can comprise at least one hydrocarbon containing from 7 to 9 carbon atoms.

In an alternative embodiment, the instant invention provides a liquid-liquid separator interface detection system and polymerization process, in accordance with any of the preceding embodiments, except that the heavy hydrocarbon solvent does not comprise a hydrocarbon containing less than 6 carbon atoms, although residual amounts (typically less than 10000 ppm, based on total weight of heavy hydrocarbon solvent) of such hydrocarbons may be present. A "hydrocarbon," as used herein refers to an organic molecule made up of only carbon and hydrogen atoms.

In an alternative embodiment, the instant invention provides a liquid-liquid separator interface detection system and polymerization process, in accordance with any of the preceding embodiments, except that the light hydrocarbon solvent comprises at least one hydrocarbon containing from 2 to 5 carbon atoms. In one embodiment, the light hydrocarbon solvent comprises at least one hydrocarbon containing from 2 to 4 carbon atoms.

In an alternative embodiment, the instant invention provides a liquid-liquid separator interface detection system and polymerization process, in accordance with any of the preceding embodiments, except that the light hydrocarbon solvent does not comprise a hydrocarbon containing more than 5 carbon atoms, although residual amounts (typically less than 10000 ppm, based on total weight of light hydrocarbon solvent) of such hydrocarbons may be present. A "hydrocarbon," as used herein refers to an organic molecule made up of only carbon and hydrogen atoms.

In one embodiment, the light hydrocarbon solvent is selected from ethane, propane, isobutane, or isopentane, or mixtures thereof, and preferably propane or isobutane.

In one embodiment, the amount of light hydrocarbon solvent is from 5 to 40 weight percent, based on the weight of the polymer solution. All individual values and subranges from 5 to 40 weight percent are included herein and disclosed herein; for example, the amount of light hydrocarbon solvent in the polymer solution can be from a lower limit of 5, 15, 25 or 35 weight percent to an upper limit of 10, 20, 30 or 40 weight percent. For example, the amount of light hydrocarbon solvent in the polymer solution may be in the range of from 5 to 40 weight percent, or in the alternative, the amount of light hydrocarbon solvent in the polymer solution may be in the range of from 20 to 35 weight percent.

In an alternative embodiment, the instant invention provides a liquid-liquid separator interface detection system and polymerization process, in accordance with any of the preceding embodiments, except that the heavy hydrocarbon solvent is selected from n-hexane, n-heptane, n-octane, iso-octane, n-nonane, n-decane, or mixtures thereof, preferably n-octane, iso-octane, n-nonane, n-decane, or mixtures thereof, and more preferably n-octane.

In one embodiment, the solvent comprises from 20 to 50 weight percent based on the sum weight of the light hydrocarbon solvent and the heavy hydrocarbon solvent. All individual values and subranges from 20 to 50 weight percent are included herein and disclosed herein; for example, the amount of light hydrocarbon solvent based on the sum weight of the light hydrocarbon solvent and the heavy hydrocarbon solvent can be from a lower limit of 20, 30, or 40 weight percent to an upper limit of 25, 35, 45, or 50 weight percent. For example, the amount of light hydrocarbon solvent based on the sum weight of the light hydrocarbon solvent and the heavy hydrocarbon solvent may be in the range of from 20 to 50 weight percent, or in the alternative, from 20 to 40 weight percent.

In an alternative embodiment, the instant invention provides a liquid-liquid separator interface detection system and polymerization process, in accordance with any of the preceding embodiments, except that the light hydrocarbon solvent comprises a C3 hydrocarbon, and the heavy hydrocarbon solvent comprises a hydrocarbon with 8 or more carbon atoms.

In an alternative embodiment, the instant invention provides a liquid-liquid separator interface detection system and polymerization process, in accordance with any of the preceding embodiments, except that the light hydrocarbon solvent comprises a C3 hydrocarbon, and the heavy hydrocarbon solvent comprises a hydrocarbon with 10 or more carbon atoms.

In an alternative embodiment, the instant invention provides a liquid-liquid separator interface detection system and polymerization process, in accordance with any of the preceding embodiments, except that there is no special operation (like distillation), in the polymerization process, to separate heavy and light hydrocarbon components of the solvent from each other.

In an alternative embodiment, the instant invention provides a liquid-liquid separator interface detection system and polymerization process, in accordance with any of the preceding embodiments, except that there is no special unit operation (such as distillation), in the polymerization process, to separate the solvent from the monomers and co-monomers.

In an alternative embodiment, the instant invention provides a liquid-liquid separator interface detection system and polymerization process, in accordance with any of the preceding embodiments, except that there is no special unit operation (such as distillation), in the polymerization process, to separate the solvent from the polymers.

In an alternative embodiment, the instant invention provides a liquid-liquid separator interface detection system and polymerization process, in accordance with any of the preceding embodiments, except that, in step B, the polymer concentration in the polymer solution entering the liquid-liquid separator is from 5 to 30 weight percent, based on the weight of the polymer solution. All individual values and subranges from 5 to 30 weight percent of the polymer solution are included herein and disclosed herein; for example, the polymer concentration in the polymer solution can be from a lower limit of 5, 15, or 25 weight percent to an upper limit of 10, 20 or 30 weight percent. For example, the polymer concentration in the polymer solution may be in the range of from 5 to 30 weight percent, or in the alternative, the polymer concentration in the polymer solution may be in the range of from 10 to 15 weight percent, or in the alternative, the polymer concentration in the polymer solution may be in the range of from 15 to 20 weight percent.

In an alternative embodiment, the instant invention provides a liquid-liquid separator interface detection system and polymerization process, in accordance with any of the preceding embodiments, except that, in step B, the polymer concentration in the polymer in the polymer-rich phase exiting the liquid-liquid separator is from 20 to 50 weight percent. All individual values and subranges from 20 to 50 weight percent are included herein and disclosed herein; for example, the polymer concentration in the polymer in the polymer-rich phase exiting the liquid-liquid separator can be from a lower limit of 20, 30, 40 or 45 weight percent to an upper limit of 25, 35, 45 or 50 weight percent. For example, the polymer concentration in the polymer in the polymer-rich phase exiting the liquid-liquid separator may be in the range of from 20 to 50 weight percent, or in the alternative, the polymer concentration in the polymer in the polymer-rich phase exiting the liquid-liquid separator may be in the range of from 35 to 50 weight percent, or in the alternative, the polymer concentration in the polymer in the polymer-rich phase exiting the liquid-liquid separator may be in the range of from 20 to 35 weight percent, or in the alternative, the polymer concentration in the polymer in the polymer-rich phase exiting the liquid-liquid separator may be in the range of from 30 to 40 weight percent.

In an alternative embodiment, the instant invention provides a liquid-liquid separator interface detection system and polymerization process, in accordance with any of the preceding embodiments, except that no heat is added between each reactor and the liquid-liquid separator.

In an alternative embodiment, the instant invention provides a liquid-liquid separator interface detection system and polymerization process, in accordance with any of the preceding embodiments, except that the process does not contain a heating device, such as a heat exchanger between step A and step B.

In an alternative embodiment, the instant invention provides a liquid-liquid separator interface detection system and polymerization process, in accordance with any of the preceding embodiments, except that no heat is added to the polymer solution in step A and step B, by means of a heat exchanger.

In an alternative embodiment, the instant invention provides a liquid-liquid separator interface detection system and polymerization process, in accordance with any of the preceding embodiments, except that no heat is added to the polymer solution in step A and step B, by means of a higher temperature stream (higher energy).

In an alternative embodiment, the instant invention provides a liquid-liquid separator interface detection system and polymerization process, in accordance with any of the preceding embodiments, except that step B is not repeated.

In an alternative embodiment, the instant invention provides a liquid-liquid separator interface detection system and polymerization process, in accordance with any of the preceding embodiments, except that step B is repeated.

In an alternative embodiment, the instant invention provides a liquid-liquid separator interface detection system and polymerization process, in accordance with any of the preceding embodiments, except that, in step B, the polymer solution forms only two liquid phases.

In an alternative embodiment, the instant invention provides a liquid-liquid separator interface detection system and polymerization process, in accordance with any of the preceding embodiments, except that, no light hydrocarbon solvent is added to step B.

In an alternative embodiment, the instant invention provides a liquid-liquid separator interface detection system and polymerization process, in accordance with any of the preceding embodiments, except that, light hydrocarbon solvent is added to step B.

In an alternative embodiment, the instant invention provides a liquid-liquid separator interface detection system and polymerization process, in accordance with any of the preceding embodiments, except that one or more phase separation agents are added to the polymer solution prior to, or within, the liquid-liquid separator.

In an alternative embodiment, the instant invention provides a liquid-liquid separator interface detection system and polymerization process, in accordance with any of the preceding embodiments, except that no phase separation agent is added to the polymer solution prior to, or within, the liquid-liquid separator. In a further embodiment, no phase separation agent is added to the polymer solution after the liquid-liquid separator.

Some examples of phase separation agents include $H_2$, $N_2$, $CO$, $CO_2$, $C_3H_8$ and $CH_4$.

In an alternative embodiment, the instant invention provides a liquid-liquid separator interface detection system and polymerization process, in accordance with any of the preceding embodiments, except that the polymer-rich phase does not contain more than 5 weight percent entrained "solvent-rich phase," based on sum weight of these two phases.

In an alternative embodiment, the instant invention provides a liquid-liquid separator interface detection system and polymerization process, in accordance with any of the preceding embodiments, except that, in step B, the pressure in the liquid-liquid separator is less than, or equal to, 800 psig. All individual values and subranges from less than, or equal to, 800 psig are included herein and disclosed herein; for example, the pressure in the liquid-liquid separator can be from an upper limit of 800 psig. For example, the pressure in the liquid-liquid separator can be from an upper limit of 700 psig, or in the alternative, the pressure in the liquid-liquid separator can be from an upper limit of 600 psig.

In an alternative embodiment, the instant invention provides a liquid-liquid separator interface detection system and polymerization process, in accordance with any of the preceding embodiments, except that, in step B, the pressure in the liquid-liquid separator is from 400 psig to 800 psig.

In an alternative embodiment, the instant invention provides a liquid-liquid separator interface detection system and polymerization process, in accordance with any of the preceding embodiments, except that the pressure in the liquid-liquid separator is from 450 psig to 700 psig.

In an alternative embodiment, the instant invention provides a liquid-liquid separator interface detection system and polymerization process, in accordance with any of the preceding embodiments, except that the pressure in the liquid-liquid separator is from 500 psig to 600 psig.

In an alternative embodiment, the instant invention provides a liquid-liquid separator interface detection system and polymerization process, in accordance with any of the preceding embodiments, except that the temperature in the liquid-liquid separator is greater than, or equal to, 150° C. All individual values and subranges from greater than, or equal to, 150° C. are included herein and disclosed herein. For example, the temperature in the liquid-liquid separator can be from an upper limit of 150° C., or in the alternative, the temperature in the liquid-liquid separator can be from an upper limit of 160° C., or in the alternative, the temperature in the liquid-liquid separator can be from an upper limit of 170° C.

In an alternative embodiment, the instant invention provides a liquid-liquid separator interface detection system and polymerization process, in accordance with any of the preceding embodiments, except that, in step B, the temperature in the liquid-liquid separator is from 150° C. to 220° C.

In an alternative embodiment, the instant invention provides a liquid-liquid separator interface detection system and polymerization process, in accordance with any of the preceding embodiments, except that the temperature in the liquid-liquid separator is from 160° C. to 210° C.

In an alternative embodiment, the instant invention provides a liquid-liquid separator interface detection system and polymerization process, in accordance with any of the preceding embodiments, except that the temperature in the liquid-liquid separator is from 165° C. to 205° C.

In an alternative embodiment, the instant invention provides a liquid-liquid separator interface detection system and polymerization process, in accordance with any of the preceding embodiments, except that the liquid-liquid separator is a vessel.

In an alternative embodiment, the instant invention provides a liquid-liquid separator interface detection system and polymerization process, in accordance with any of the preceding embodiments, except that the liquid-liquid separator has a capacity greater than, or equal to, 10 gallons.

In an alternative embodiment, the instant invention provides a liquid-liquid separator interface detection system and polymerization process, in accordance with any of the preceding embodiments, except that the liquid-liquid separator has a capacity greater than, or equal to, 100 gallons.

In an alternative embodiment, the instant invention provides a liquid-liquid separator interface detection system and polymerization process, in accordance with any of the preceding embodiments, except that the liquid-liquid separator has a capacity greater than, or equal to, 1000 gallons.

In an alternative embodiment, the instant invention provides a liquid-liquid separator interface detection system and polymerization process, in accordance with any of the preceding embodiments, except that the liquid-liquid separator has a capacity greater than, or equal to, 10,000 gallons.

In an alternative embodiment, the instant invention provides a liquid-liquid separator interface detection system and polymerization process, in accordance with any of the preceding embodiments, except that the liquid-liquid separator has a capacity greater than, or equal to, 50,000 gallons.

In one embodiment, the liquid-liquid separator has a capacity from 10 to 50,000 gallons. In one embodiment, the liquid-liquid separator has a capacity from 100 to 25,000 gallons. In a preferred embodiment, no mechanical mixing takes place in the liquid-liquid separator.

In an alternative embodiment, the instant invention provides a liquid-liquid separator interface detection system and polymerization process, in accordance with any of the preceding embodiments, except that the liquid-liquid separator, in step B, contains at least two liquid phases. A liquid phase has a density greater than, or equal to, 0.2 g/cc, preferably greater than, or equal to, 0.3 g/cc, as determined gravimetrically.

The liquid-liquid separator may comprise a combination of two or more embodiments as described herein.

In an alternative embodiment, the instant invention provides a liquid-liquid separator interface detection system and polymerization process, in accordance with any of the preceding embodiments, except that the solvent-rich phase comprises less than 1000 ppm polymer. All individual values and subranges from less than 1000 ppm polymer are included herein and disclosed herein; for example, the amount of polymer in the solvent rich phase can be from an upper limit of 250, 350, 450, 550, 650, 750, 850, 950, or 1000 ppm.

In an alternative embodiment, the instant invention provides a liquid-liquid separator interface detection system and polymerization process, in accordance with any of the preceding embodiments, except that step (A) occurs in a solution polymerization reactor.

In an alternative embodiment, the instant invention provides a liquid-liquid separator interface detection system and polymerization process, in accordance with any of the preceding embodiments, except that step (A) occurs in a continuously stirred tank reactor.

In an alternative embodiment, the instant invention provides a liquid-liquid separator interface detection system and polymerization process, in accordance with any of the preceding embodiments, except that the polymerization process further comprises calculating a vertical position of the interface face from a reflected sonic signal received by the sonic transponder.

In an alternative embodiment, the instant invention provides a liquid-liquid separator interface detection system and polymerization process, in accordance with any of the preceding embodiments, except that the polymerization process further comprises adjusting a flow rate by removing one or both of the solvent-rich and the polymer-rich phases based upon the vertical position of the interface.

FIG. 1 is a schematic of a liquid-liquid separator 1 having two sonic transponders, 2 and 4. The liquid-liquid separator 1 includes a solvent rich phase 6 and a polymer rich phase 8. As shown in FIG. 1, the sonic transponders 2 and 4 are each positioned such that the sound wave from each transponder is at a right angle to the liquid-liquid interface. Polymer solution from a polymerization reactor enters the liquid-liquid separator 1 through inlet 10.

The term "polymer," as used herein, refers to a polymeric compound prepared by polymerizing monomers, whether of the same or a different type. The generic term polymer thus embraces the term homopolymer (employed to refer to polymers prepared from only one type of monomer), and the term interpolymer as defined hereinafter. The term "interpolymer," as used herein, refers to polymers prepared by the polymerization of at least two different types of monomers. The generic term interpolymer thus includes copolymers (employed to refer to polymers prepared from two different types of monomers), and polymers prepared from more than two different types of monomers.

The term "olefin-based polymer," as used herein, refers to a polymer that contains at least a majority weight percent, based on the weight of the polymer, polymerized olefin (for example, ethylene or propylene), and, optionally, one or more additional comonomers.

The term "ethylene-based polymer," as used herein, refers to a polymer that contains at least a majority weight percent polymerized ethylene (based on the weight of polymer), and, optionally, one or more additional comonomers.

The term "propylene-based polymer," as used herein, refers to a polymer that contains at least a majority weight percent polymerized propylene (based on the weight of polymer), and, optionally, one or more additional comonomers.

The term "polymer-rich phase," as used herein, in relation to two or more phases under consideration, refers to the phase containing the greater concentration of polymer, as measured by its weight fraction, based on the total weight of the polymer-rich phase.

The term "solvent-rich phase," as used herein, in relation to two or more phases under consideration, refers to the phase containing the greater concentration of solvent as measured by its weight fraction, based on total weight of the solvent-rich phase.

The term "heavy hydrocarbon solvent," as used herein, refers to a non-reactive (with respect to polymerization catalyst) hydrocarbon, containing at least one hydrocarbon containing six or more carbon atoms. Typically, heavy hydrocarbon solvents have a normal boiling point higher than 95° C. The heavy hydrocarbon solvent does not comprise a hydrocarbon containing less than six carbon atoms, although residual amounts (typically less than 10000 ppm, based on total weight of heavy hydrocarbon solvent) of such hydrocarbons may be present. A "hydrocarbon," as used herein refers to an organic molecule made up of only carbon and hydrogen atoms. Examples are alkanes like n-octane, n-nonane, iso-octane, and alkenes like internal isomers of octene (those with double bond not located on a terminal carbon atom).

The term "light hydrocarbon solvent," as used herein, refers to a non-reactive (with respect to polymerization catalyst) hydrocarbon, containing at least one hydrocarbon containing five or less carbon atoms. Typically, light hydrocarbon solvents have a normal boiling point lower than 40° C. The light hydrocarbon solvent does not comprise a hydrocarbon containing more than five carbon atoms, although residual amounts (typically less than 10000 ppm, based on total weight of light hydrocarbon solvent) of such hydrocarbons may be present. A "hydrocarbon," as used herein refers to an organic molecule made up of only carbon and hydrogen atoms. Examples include ethane, propane, isobutene, and the like.

A phase, as used herein, refers to is a region of space (a thermodynamic system), throughout which all physical properties of a material are essentially uniform. Examples of physical properties include density, index of refraction, and chemical composition.

A liquid-liquid phase is a combination of two separate liquid phases which are not miscible.

The term "liquid-liquid separator (LLS)," as used herein, refers to a device used for the separation of two or more liquid phases. The separation results from the specific action, for example, a reduction in pressure, taken to induce two or more liquid phases.

The term "polymer solution," as used herein, refers to the complete dissolution of polymer in one or more solvents (typically much lower in molecular weight than polymer) to form a homogeneous (most often in liquid state) phase. The solution comprises the polymer and solvent, and may also comprise unreacted monomers and other residuals of the polymerization reaction.

The term "solvent," as used herein, refers to a substance (for example, a hydrocarbon or a mixture of two or more hydrocarbons (excluding monomer and comonomer)) that dissolves a species of interest, like a monomer and/or polymer, resulting in a liquid phase.

The term "mixed solvent," as used herein, refers to a mixture of two or more solvents (for example, a mixture of two or more hydrocarbons).

The term "single solvent," as used herein, refers to one solvent (for example, one hydrocarbon).

The term "solution polymerization," as used herein, refers to a polymerization process in which the formed polymer is dissolved in the polymerization solvent.

The term "phase separation agent," as used herein, refers to a substance, which, when added to an existing polymer solution, has the effect of lowering the Lower Critical Solution Temperature (LCST) at a given polymer weight fraction.

Lower Critical Solution Temperature (LCST), as used herein, is defined as the temperature, above which, a solution of fixed composition, at a fixed pressure, separates into two liquid phases, and, below this temperature, the solution exists as a single liquid phase.

The term "polymerization system," as used herein, refers to a mixture comprising monomers, solvent and catalyst, and which will undergo polymerization reaction under appropriate conditions. The polymerization system corresponds to the total feed to the reactor.

The term "adiabatic reactor," as used herein, refers to a reactor which has no active heat removal mechanism and no active heat addition mechanism.

The term "pressure reducing means," as used herein, refers to a device, such as a control valve, that allows reduction in pressure of a continuous stream of liquid or a fixed batch of liquid.

The phrase "actively reduced in a controlled manner," as used herein, refers to an action, such as the use of a control valve, to reduce pressure to a desired level and at a desired rate.

The term "single phase polymer solution," as used herein, refers to the complete dissolution of polymer in one or more solvents (typically much lower in molecular weight than polymer) to form a homogeneous (most often in liquid state) phase.

The phrase "concentration of polymer in the polymer-rich phase," as used herein, refers to the weight fraction of the polymer, based on the total weight of the solution containing the polymer (polymer-rich phase).

The phrase "concentration of polymer in the solvent-rich phase," as used herein, refers to the weight fraction of the polymer, based on the total weight of the solution containing the polymer (solvent-rich phase).

The term "subcritical region," as defined herein, refers to a polymerization temperature below the critical temperature of the polymerization medium (defined as the mixture of solvent(s), monomer and comonomer(s) [no catalyst(s) or cocatalyst(s)]), and a polymerization pressure below the critical pressure of the polymerization medium.

The term "critical temperature," as used herein, refers to the temperature of the polymerization medium, above which, the polymerization medium does not phase separate, regardless of any pressure change.

The term "critical pressure," as used herein, refers to the pressure of the polymerization medium, above which, the polymerization medium does not phase separate, regardless of any temperature change.

The term "cloud point pressure" is the pressure, below which, the polymer solution of a fixed composition at a fixed temperature, separates into two liquid phases. Above this pressure, the polymer solution is a single liquid phase.

"Cloud point temperature" is the temperature above (threshold temperature) which, the polymer solution of a fixed composition at a fixed pressure, separates into two liquid phases. Below this temperature, the polymer solution is a single liquid phase. In addition, the cloud point temperature may also be a ceiling temperature, below which, two phases exist, and above which, one phase exists.

EXAMPLES

Figure 2:
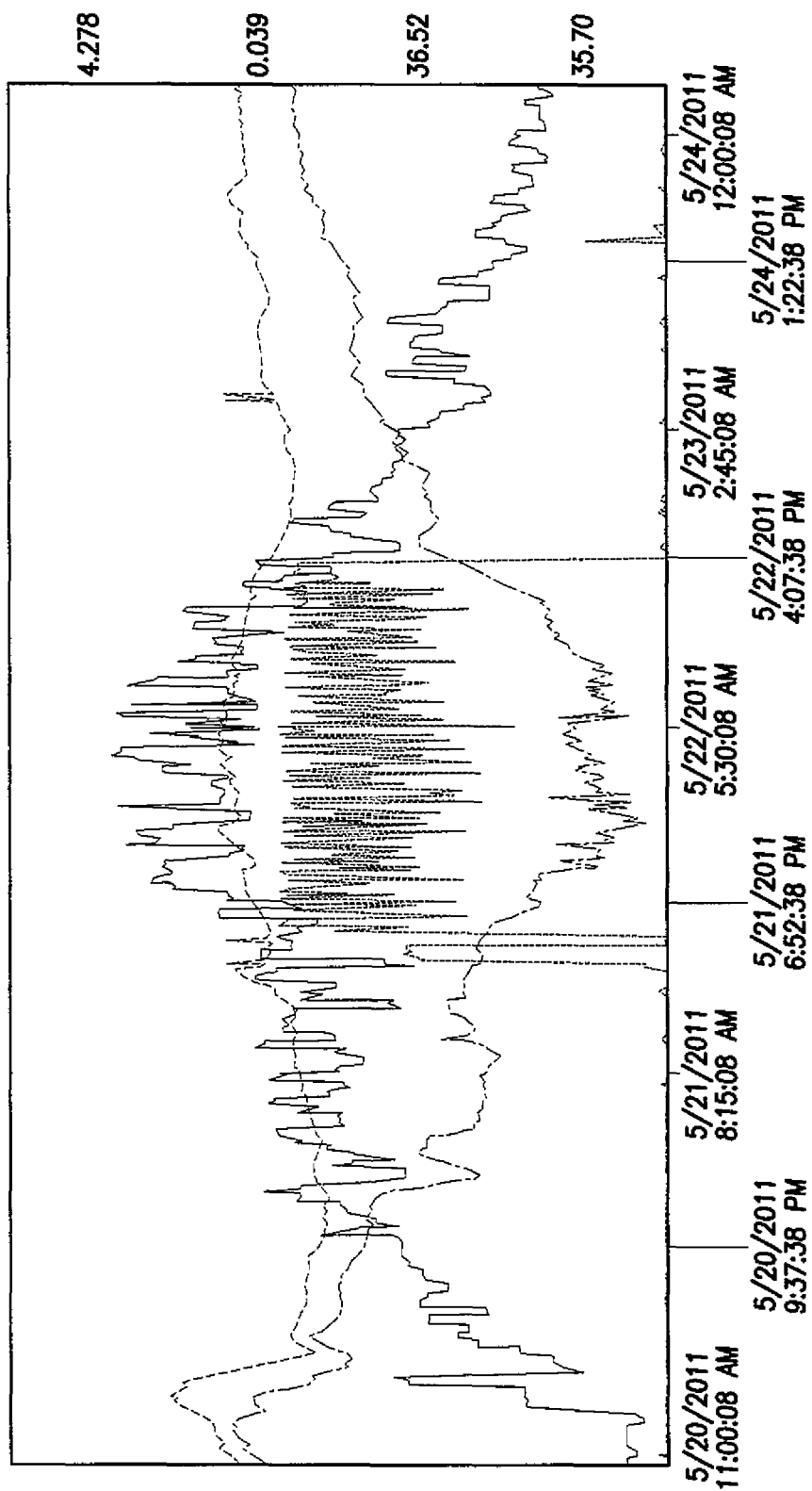
FIG. 2 is a graph demonstrating the changes of solution densities of the solvent rich and polymer rich phases as a function of separation agent concentration upon the occurrence of liquid-liquid separation, and the ability of the sonic transponder to detect the presence of a liquid liquid interface between the two phases upon the formation of two liquid phases.

The following examples illustrate the present invention but are not intended to limit the scope of the invention. FIG. 2 illustrates the separation of a solvent rich phase and a polymer rich phase, as detected by an INTERFAZER sonic transponder. The polymer solution from a single solution continuously stirred reactor for production of a semi-crystalline, very low diene-containing ethylene-propylene-diene terpolymer (EPDM) was used to produce the information in FIG. 2. High reactor pressure was used to ensure a single liquid phase environment for homogeneous polymerization. The pressure of the polymer solution was quickly reduced from 2200 psig to 800 psig as the polymer solution passed through the reactor pressure control valve. The resulting density of the polymer-rich stream after liquid-liquid separation was predicted, using VXLE modeling software from VXLE ApS (Copenhagen, Denmark) to be 35.5 lbs/ft$^3$ at 185° C. and 783 psig with a solution density differential between the polymer rich and solvent rich phases of 9 lbs/ft$^3$. FIG. 2 shows the phase separation as a function of time and phase separation agent concentration. On FIG. 2, the far left position indicates the start time for injection of a phase separation agent. At that point, the densities of the polymer rich phase and the solvent rich phase are very close to each other and to the reactor effluent (polymer solution) density. Propane, a separation agent, is fed into the liquid-liquid separator beginning at the time indicated by the far left of the y-axis. As the propane concentration in the liquid-liquid separator increases, the solution density of the solvent rich phase decreases. At a propane concentration of 13%, the solvent rich phase shows a rapid decrease in density. At that same propane concentration, the sonic transponder shows a 40 to 50% liquid liquid interface level ("1$^{st}$ big density drop"). Upon reaching 15% propane, propane level was maintained constant during which time the density difference was maintained and the sonic transponder showed a clear interface. Subsequently, the propane was removed. Upon dropping below 13% propane, the viscosities of the polymer rich and solvent rich phases approached each other and the sonic transducer did not show clear phase separation. In FIG. 2, the long dashed line indicates the polymer rich phase density, the dash-dot-dash line indicates the solvent rich phase density, the solid line indicates the propane content, and the sonic transponder signal is indicated by the dotted line.

The present invention may be embodied in other forms without departing from the spirit and the essential attributes thereof, and, accordingly, reference should be made to the appended claims, rather than to the foregoing specification, as indicating the scope of the invention.

We claim:

1. A solvent based solution polymerization process comprising:
    A) solution polymerizing in a solution polymerization reactor one or more monomers in the presence of a solvent, to form a polymer solution;
    B) transferring the polymer solution from the solution polymerization reactor to a liquid-liquid separator vessel, without adding heat to the solution, and wherein a pressure of the polymer solution is actively reduced in a controlled manner prior to, or within, the liquid-liquid separator vessel, to induce at least two liquid phases, a polymer-rich phase and a solvent-rich phase, and wherein a concentration of polymer in the polymer-rich phase is higher than that in the polymer solution transferred to the liquid-liquid separator vessel from the solution polymerization reactor; and
    C) detecting an interface between the polymer-rich phase and the solvent-rich phase by use of two sonic transponders—a first sonic transponder and a second sonic transponder positioned within the liquid-liquid separator vessel;
        where the first sonic transponder sends a first sonic signal from a top of the liquid-liquid separator vessel and for receiving a first reflected portion of the sonic signal; and
        where the second sonic transponder sends a second sonic signal from a bottom of the liquid-liquid separator vessel and for receiving a second reflected portion of the sonic signal; where the first reflected portion of the first sonic signal is created by reflecting a first portion of the first sonic signal from a liquid-liquid interface between the solvent rich phase and the polymer rich phase; and wherein the second reflected portion of the second sonic signal is created by reflecting a second portion of the second sonic signal from the liquid-liquid interface between the solvent rich phase and the polymer rich phase; wherein the first sonic transponder is positioned such that it transmits the first sonic signal perpendicularly to the liquid-liquid interface and wherein the second sonic transponder is positioned such that it transmits the second sonic signal perpendicularly to the liquid-liquid interface; and
    D) removing one or both of the solvent-rich phase and the polymer-rich phase.

2. The polymerization process according to claim 1, wherein the solvent-rich phase is removed from the liquid-liquid separator vessel and the removed solvent-rich phase comprises less than 1000 ppm polymer.

3. The polymerization process according to claim 1, wherein step (A) occurs in a solution polymerization reactor.

4. The polymerization process according to claim 1, wherein step (A) occurs in a continuously stirred tank reactor.

5. The polymerization process according to claim 1, further comprising calculating a vertical position of the interface face from a reflected sonic signal received by the sonic transponder.

6. The polymerization process according to claim 1, further comprising adjusting a flow rate of removing one or both of the solvent-rich and the polymer-rich phases based upon the vertical position of the interface.

* * * * *